US012805930B2

(12) United States Patent
Altmann et al.

(10) Patent No.: US 12,805,930 B2
(45) Date of Patent: Nov. 24, 2026

(54) BIPOLAR TISSUE ABLATION IN ACCORDANCE WITH A PREDEFINED PERIODIC SET OF TIME SLOTS

(71) Applicant: BIOSENSE WEBSTER (ISRAEL) LTD., Yokneam (IL)

(72) Inventors: Andres Claudio Altmann, Haifa (IL); Assaf Govari, Haifa (IL); Ella Ozeri, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 216 days.

(21) Appl. No.: 18/216,165

(22) Filed: Jun. 29, 2023

(65) Prior Publication Data

US 2023/0346467 A1 Nov. 2, 2023

Related U.S. Application Data

(63) Continuation of application No. 16/920,865, filed on Jul. 6, 2020, now abandoned.

(51) Int. Cl.

| | |
|---|---|
| ***A61B 18/14*** | (2006.01) |
| *A61B 18/00* | (2006.01) |
| *A61B 18/12* | (2006.01) |

(52) U.S. Cl.

CPC ..................... *A61B 18/1492* (2013.01); *A61B 2018/00351* (2013.01); *A61B 2018/00577* (2013.01);

(Continued)

(58) Field of Classification Search

CPC ...... A61B 18/1492; A61B 2018/00351; A61B 2018/00577; A61B 2018/00613;

(Continued)

(56) References Cited

U.S. PATENT DOCUMENTS

| | | | |
|---|---|---|---|
| 5,391,199 | A | 2/1995 | Ben-Haim |
| 6,239,724 | B1 | 5/2001 | Doron et al. |

(Continued)

FOREIGN PATENT DOCUMENTS

| | | | |
|---|---|---|---|
| CN | 206453845 | U | 9/2017 |
| RU | 2665627 | C2 | 9/2018 |

(Continued)

OTHER PUBLICATIONS

European Search Report for corresponding EPA No. 21165823.2 dated Sep. 21, 2021.

(Continued)

*Primary Examiner* — Beverly M Flanagan
*Assistant Examiner* — Abigail M Ziegler
(74) *Attorney, Agent, or Firm* — Dergosits & Noah LLP; Todd A. Noah

(57) ABSTRACT

A method for applying bipolar ablation pulses, the method includes positioning multiple electrodes of a catheter in contact with tissue of an organ. The tissue is ablated using the multiple electrodes in accordance with a predefined pattern including a periodic set of time slots. Each of the time slots defines (i) an electrode-pair (EP), (ii) a waveform of one or more bipolar ablation pulses (BAPs) applied to the tissue by the EP, and (iii) a duration of the time slot. The time slots are applied sequentially, and the pattern further includes at least one time slot that is empty.

20 Claims, 2 Drawing Sheets

(52) U.S. Cl.
CPC ............... *A61B 2018/00613* (2013.01); *A61B 2018/00761* (2013.01); *A61B 2018/124* (2013.01); *A61B 2018/126* (2013.01); *A61B 2018/1407* (2013.01); *A61B 2018/1467* (2013.01)

(58) Field of Classification Search
CPC .... A61B 2018/00761; A61B 2018/124; A61B 2018/126; A61B 2018/1407; A61B 2018/1467; A61B 2018/00357
See application file for complete search history.

(56) References Cited

U.S. PATENT DOCUMENTS

| | | | |
|---|---|---|---|
| 6,332,089 | B1 | 12/2001 | Acker et al. |
| 6,484,118 | B1 | 11/2002 | Govari |
| 6,618,612 | B1 | 9/2003 | Acker et al. |
| 6,635,056 | B2 | 10/2003 | Kadhiresan |
| 6,690,963 | B2 | 2/2004 | Ben-Haim et al. |
| 8,048,067 | B2 | 11/2011 | Davalos |
| 8,221,411 | B2 | 7/2012 | Francishelli |
| 10,271,893 | B2 | 4/2019 | Stewart |
| 10,342,598 | B2 | 7/2019 | Long |
| 10,470,822 | B2 | 11/2019 | Garcia |
| 10,531,914 | B2 | 1/2020 | Stewart |
| 11,033,236 | B2 | 6/2021 | Viswanathan et al. |
| 11,259,869 | B2 | 3/2022 | Mickelsen |
| 2002/0065455 | A1 | 5/2002 | Ben-Haim et al. |
| 2003/0069573 | A1 | 4/2003 | Kadhiresan et al. |
| 2003/0120150 | A1 | 6/2003 | Govari |
| 2004/0068178 | A1 | 4/2004 | Govari |
| 2016/0051324 | A1 | 2/2016 | Stewart |
| 2016/0166310 | A1 | 6/2016 | Stewart et al. |
| 2017/0065339 | A1 | 3/2017 | Mickelsen |
| 2017/0189097 | A1* | 7/2017 | Viswanathan ......... A61N 1/362 |
| 2018/0214202 | A1 | 8/2018 | Howard et al. |
| 2018/0235495 | A1 | 8/2018 | Rubenstein |
| 2019/0183378 | A1 | 6/2019 | Mosesov et al. |
| 2019/0223938 | A1 | 7/2019 | Arena |
| 2019/0336207 | A1 | 11/2019 | Viswanathan |
| 2021/0161582 | A1* | 6/2021 | Byrd .................. A61B 18/1206 |
| 2021/0315639 | A1 | 10/2021 | Manucherhabadi et al. |
| 2022/0000543 | A1 | 1/2022 | Altmann et al. |
| 2022/0133403 | A1* | 5/2022 | Olson ................ A61B 18/1492 606/41 |
| 2023/0172650 | A1* | 6/2023 | Castellvi ............ A61B 18/1492 606/32 |

FOREIGN PATENT DOCUMENTS

| | | | |
|---|---|---|---|
| WO | 9605768 | A1 | 2/1996 |
| WO | 2015103530 | A1 | 7/2015 |
| WO | WO2016132339 | A1 | 8/2016 |
| WO | 2017024123 | A1 | 2/2017 |
| WO | WO2017119934 | A1 | 7/2017 |
| WO | WO2018208795 | A1 | 11/2018 |
| WO | WO2019217433 | A1 | 11/2019 |

OTHER PUBLICATIONS

European Examination Report for corresponding EPA No. 21165823.2 dated Oct. 16, 2024.

* cited by examiner

BIPOLAR TISSUE ABLATION IN ACCORDANCE WITH A PREDEFINED PERIODIC SET OF TIME SLOTS

CROSS-REFERENCE TO RELATED APPLICATION

This application is a continuing application of U.S. application Ser. No. 16/920,865 filed Jul. 6, 2020, which is incorporated herein by reference.

FIELD OF THE INVENTION

The present invention relates generally to medical devices, and particularly to methods and systems for bipolar tissue ablation.

BACKGROUND OF THE INVENTION

Various techniques for ablating an extended area of heart tissue by applying irreversible electroporation (IRE) pulses are known in the art.

For example, U.S. Pat. No. 10,470,822 describes a system for estimating a three-dimensional treatment volume for a device that applies treatment energy through a plurality of electrodes defining a treatment area, the system comprising a memory, a display device, a processor coupled to the memory and the display device, and a treatment planning module stored in the memory and executable by the processor.

U.S. Patent Application Publication No. 2019/0336207 describes a system that includes a pulse waveform generator and an ablation device coupled to the pulse waveform generator. The ablation device includes at least one electrode configured for ablation pulse delivery to tissue during use. The pulse waveform generator is configured to deliver voltage pulses to the ablation device in the form of a pulsed waveform. The pulsed waveform can include multiple levels of hierarchy, and multiple sets of electrodes can be activated such that their pulsed delivery is interleaved with one another.

SUMMARY OF THE INVENTION

An embodiment of the present invention that is described herein provides a method for applying bipolar ablation pulses, the method includes positioning multiple electrodes of a catheter in contact with tissue of an organ. The tissue is ablated using the multiple electrodes in accordance with a predefined pattern including a periodic set of time slots. Each of the time slots defines (i) an electrode-pair (EP), (ii) a waveform of one or more bipolar ablation pulses (BAPs) applied to the tissue by the EP, and (iii) a duration of the time slot. The time slots are applied sequentially, and the pattern further includes at least one time slot that is empty.

In some embodiments, a first electrode of a first EP is positioned between second and third electrodes of a second EP. In other embodiments, each of the time slots includes a time gap scheduled before or after the one or more BAPs. In yet other embodiments, the BAPs include irreversible electroporation (IRE) BAPs.

In an embodiment, the EPs of the time slots have a same inter-electrode distance. In another embodiment, a first EP of a first time slot of the predefined pattern includes a first electrode and a second electrode, and a second EP of a second time slot of the predefined pattern includes the first electrode and a third electrode.

In some embodiments, the predefined pattern includes at least one time slot positioned between the first and second time slots. In other embodiments, positioning the catheter includes positioning a lasso catheter.

There is additionally provided, in accordance with an embodiment of the present invention, a system including a catheter, a pulse generator, and a processor. The catheter including multiple electrodes, which are configured to make contact with tissue of an organ. The pulse generator is configured to generate one or more bipolar ablation pulses (BAPs). The processor is configured to ablate the tissue using the multiple electrodes in accordance with a predefined pattern including a periodic set of time slots that are applied to the tissue sequentially. Each of the time slots defines (i) an electrode-pair (EP) selected from the multiple electrodes, (ii) a waveform of the one or more BAPs applied to the tissue by the EP, and (iii) a duration of the time slot, and the pattern further includes at least one time slot that is empty.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
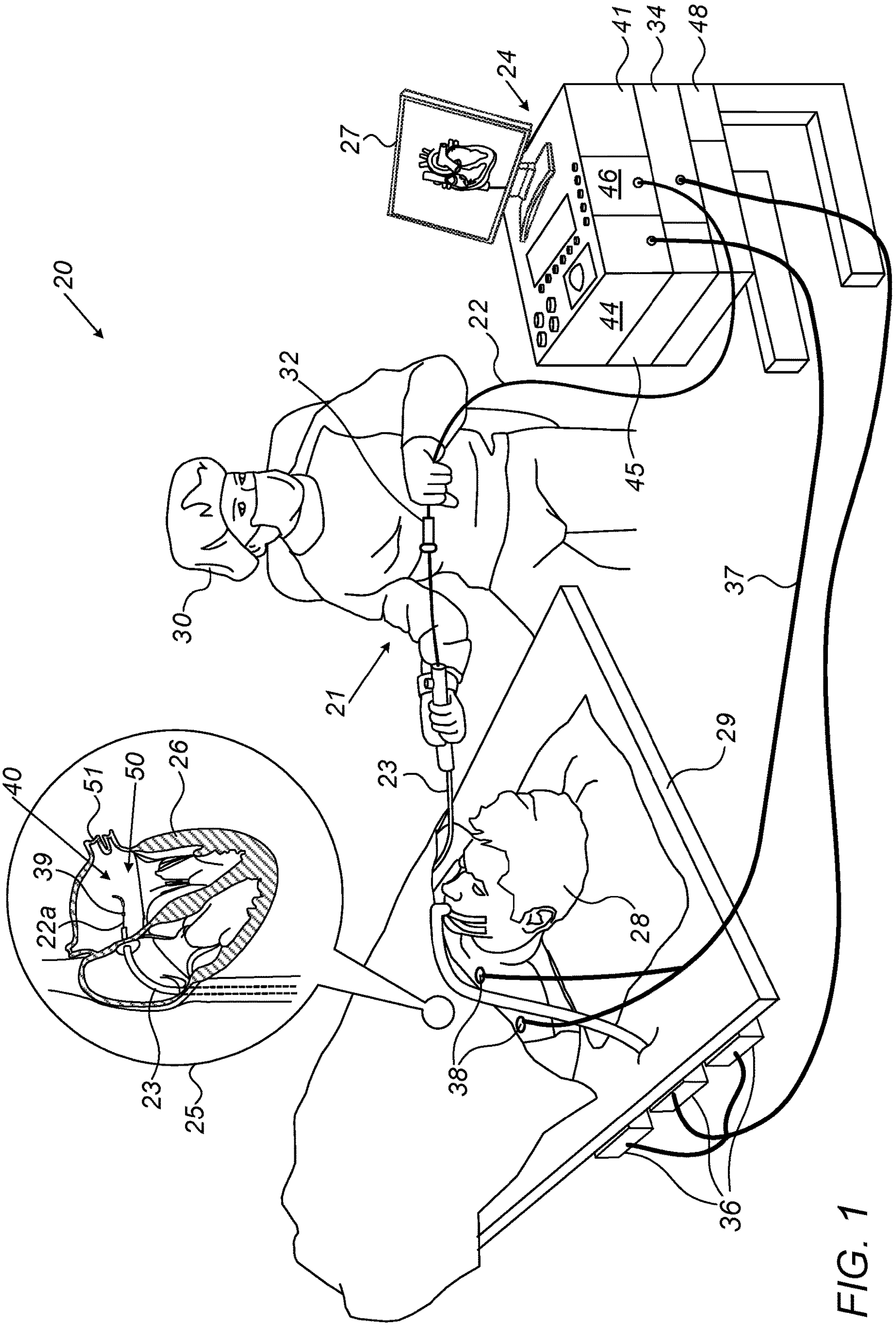
FIG. 1 is a schematic, pictorial illustration of a catheter-based position-tracking and irreversible electroporation (IRE) ablation system, in accordance with an exemplary embodiment of the present invention.

Irreversible electroporation (IRE) may be used, for example, for treating arrhythmia by ablating tissue cells using high-voltage pulses applied to the tissue. Cellular destruction occurs when the transmembrane potential exceeds a threshold, leading to cell death and formation of a lesion. In IRE-based ablation procedures, also referred to herein as an IRE ablation for brevity, high-voltage bipolar electrical pulses are applied, for example, to pairs of electrodes in contact with tissue to be ablated, so as to form a lesion between the electrodes, and thereby to treat arrhythmia in a patient heart.

Sometimes, a lasso-type catheter having multiple electrodes, may be used for performing IRE ablation over an extended area. Due to the lasso shape of the catheter, when applying bipolar IRE pulses to pairs of electrodes sequentially or simultaneously, one or more electrodes that are not intended to be energized, may undesirably touch an energized electrode, and consequently, may disrupt the outcome of the IRE ablation, and in severe cases, may be harmful to the patient.

Embodiments of the present invention that are described hereinbelow provide improved techniques for applying the IRE bipolar pulses using an ablation protocol that improves the patient safety.

In some embodiments, in an IRE ablation procedure using a lasso-type catheter, a physician positions multiple electrodes of the catheter in contact with a target tissue, such as pulmonary vein of a patient heart. Subsequently, the physician may use a processor that controls an IRE ablation system for ablating the tissue using the multiple electrodes in accordance with a predefined pattern comprising a periodic set of time slots.

In some embodiments, the time slots are applied sequentially, and each of the time slots defines (i) an electrode-pair (EP) selected from among the multiple electrodes, (ii) a waveform of one or more bipolar ablation pulses (BAPs), also referred to herein as "IRE ablation pulses," are applied to the tissue by the EP, and (iii) duration of the time slot. Note that the term "periodic" refers to one or more repetitions of the same predefined pattern. For example, a given predefined pattern may have three time slots, wherein one or more BAPs are applied sequentially to first, second and third EPs, during first second and third time slots, respectively. Subsequently, the given predefined pattern is repeated with applying the one or more BAPs to the first EP of the first time slot and so on.

In some embodiments, the electrodes of different EPs are interleaved, such that a first electrode of a first EP is positioned between second and third electrodes of a second EP. Each of the time slots comprises a time gap scheduled before or after the one or more BAPs, so that during the time gap IRE ablation pulses are not applied to the target tissue.

In some embodiments, the pattern further may comprise at least one time slot that is empty, in other words, IRE ablation pulses are not applied to any EP during the duration of the empty time slot.

The disclosed techniques improve the safety in various bipolar ablation procedures applying bipolar pulses applied to a target tissue having a broad area, by controlling the position of the bipolar ablation pulses applied to the target tissue.

System Description

FIG. 1 is a schematic, pictorial illustration of a catheter 21 based position-tracking and irreversible electroporation (IRE) ablation system 20, in accordance with an exemplary embodiment of the present invention.

In some embodiments, system 20 comprises a deflectable tip section 40 that is fitted at a distal end 22*a* of a shaft 22 of catheter 21 with tip section 40 comprising multiple electrodes 50 (inset 25). In the present example, tip section 40 comprises a Lasso® catheter, also referred to herein as "lasso" for brevity, produced by Biosense Webster Inc. (Irvine, Calif.). The lasso and electrodes 50 are described in detail with respect to FIG. 2 below.

In other embodiments, tip section 40 may comprise any other suitable type of deflectable catheter having electrodes 50.

In the embodiment described herein, electrodes 50 are configured to apply IRE ablation pulses to tissue of the left atrium of a heart 26, such as IRE ablation of an ostium 51 of a pulmonary vein in heart 26. Electrodes 50 may also be used for sensing intra-cardiac electrocardiogram (ECG) signals. Note that the techniques disclosed herein are applicable, mutatis mutandis, to other sections (e.g., atrium or ventricle) of heart 26, and to other organs of a patient 28.

In some embodiments, the proximal end of catheter 21 is connected to a control console 24 (also referred to herein as a console 24) comprising an ablative power source, in the present example an IRE pulse generator (IPG) 45, which is configured to deliver peak power in the range of tens of kW. Console 24 comprises a switching box 46, which is configured to switch the power applied by IPG 45 to one or more selected pairs of electrodes 50. A sequenced IRE ablation protocol, also referred to herein as an ablation plan or a predefined pattern, may be defined in advance by physician 30, or by processor 41, or by a combination thereof, and stored in a memory 48 of console 24.

In some embodiments, processor 41 and/or physician 30 may select, e.g., based on electrical mapping of activation pulses produced in heart 26, the most suitable predefined pattern for obtaining the desired outcome of the IRE ablation procedure. The configuration of tip section 40 with IPG 45 and switching box 46 are described in detail with respect to FIG. 2 below, and the predefined pattern is described in detail in FIGS. 2 and 3 below.

In some embodiments, a physician 30 inserts distal end 22*a* of shaft 22 through a sheath 23 into heart 26 of patient 28 lying on a table 29. Physician 30 navigates distal end 22*a* of shaft 22 to a target location in heart 26 by manipulating shaft 22 using a manipulator 32 located, for example, in close proximity to the proximal end of catheter 21. During the insertion of distal end 22*a*, deflectable tip section 40 is maintained in a straightened configuration by sheath 23. By containing tip section 40 in a straightened configuration, sheath 23 also serves to minimize vascular trauma when physician 30 moves catheter 21, through the vasculature of patient 28, to the target location, such as an ablation site in heart 26.

Once distal end 22*a* of shaft 22 has reached the ablation site, physician 30 retracts sheath 23 and manipulates shaft 22 to place electrodes 50 disposed over the lasso of tip section 40 to make contact with the walls of ostium 51 at the ablation site. In the present example, the ablation site comprises a pulmonary vein, but in other embodiments, physician 30 may select any other suitable ablation site.

In some embodiments, electrodes 50 are connected by wires running through shaft 22 to the processor 41, which is configured to control switching box 46 of interface circuits 44 in console 24.

As further shown in inset 25, distal end 22*a* comprises a position sensor 39 of a position tracking system, which is coupled to distal end 22*a*, e.g., at tip section 40. In the present example, position sensor 39 comprises a magnetic position sensor, but in other embodiments, any other suitable type of position sensor (e.g., other than magnetic-based) may be used. During the navigation of distal end 22*a* in heart 26, processor 41 of console 24 receives signals from magnetic position sensor 39 in response to magnetic fields from external field generators 36, for example, for the purpose of measuring the position of tip section 40 in heart 26 and, optionally, displays the tracked position overlaid on the image of heart 26, on a display 27 of console 24. Magnetic field generators 36 are placed at known positions external to patient 28, e.g., below table 29. Console 24 also comprises a driver circuit 34, configured to drive magnetic field generators 36.

The method of position sensing using external magnetic fields is implemented in various medical applications, for example, in the CARTO™ system, produced by Biosense Webster Inc. (Irvine, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publication Nos. 2002/0065455 A1, 2003/0120150 A1 and 2004/0068178 A1, whose disclosures are all incorporated herein by reference.

Typically, processor 41 of console 24 comprises a general-purpose processor of a general-purpose computer, with suitable front end and interface circuits 44 for receiving signals from catheter 21, as well as for applying ablation energy via catheter 21 in a left atrium of heart 26 and for controlling the other components of system 20. Processor 41 typically comprises software in memory 48 of system 20, which is programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Applying Irreversible Electroporation Pulses To Tissue

Irreversible electroporation (IRE), also referred to as Pulsed Field Ablation (PFA), may be used as a minimally invasive therapeutic modality for forming a lesion (e.g., killing tissue cells) at the ablation site by applying high-voltage pulses to the tissue. In the present example, IRE pulses may be used for killing myocardium tissue cells in order to treat cardiac arrhythmia in the heart 26. Cellular destruction occurs when the transmembrane potential exceeds a threshold, leading to cell death and thus the development of a tissue lesion. Therefore, of particular interest is the use of high-voltage bipolar electrical pulses, e.g., using a pair of electrodes 50 in contact with tissue at the ablation site, to generate high electric fields (e.g., above a certain threshold) to form a lesion by killing tissue cells located between the electrodes.

In the context of this disclosure, "bipolar" voltage pulse means a voltage pulse applied between two electrodes 50 of catheter 21 (as opposed, for example, to unipolar pulses that are applied, e.g., during a radio-frequency ablation, by a catheter electrode relative to some common ground electrode not located on the catheter). Moreover, the terms "IRE pulse" and "bipolar ablation pulse" are used interchangeably and refer to one or more bipolar pulses applied by IPG 45, via switching box 46 and an electrode-pair (EP) selected from electrodes 50, to the ablated tissue of heart 26.

To implement IRE ablation over a relatively large tissue region of heart 26, such as a circumference of an ostium of a pulmonary vein (PV) or any other suitable organ, it is necessary to use multiple pairs of electrodes 50 of catheter 21 having multi electrodes 50 in tip section 40. To make the generated electric field as spatially uniform as possible over a large tissue region it is best to have pairs of electrodes 50 selected with overlapping fields, or at least fields adjacent to each other. However, there is a Joule heating component that occurs with the IRE generated fields, and this heating may cause uncontrolled damage to tissue and undesired damage to the electrodes when multiple pairs of electrodes 50 are continuously used for applying the predefined the IRE pulses in accordance with a pattern of time slots.

In some embodiments, based on pre-mapping of activation signals produced in heart 26, processor 41 is configured to assist the physician 30 in defining the IRE ablation plan. The pre-mapping may be carried out using electrodes 50, and/or using surface electrodes 38, shown in the example of FIG. 1, as attached by wires running through a cable 37 to the chest and shoulder of patient 28.

In some embodiments, surface electrodes 38 are configured to sense body-surface (BS) ECG signals in response to beats of heart 26. Acquisition of BS ECG signals may be carried out using conductive pads attached to the body surface or any other suitable technique. As shown in FIG. 1, surface electrodes 38 are attached to the chest and shoulder of patient 28, however, additional surface electrodes 38 may be attached to other organs of patient 28, such as limbs.

In some embodiments, electrodes 50 are configured to sense intra-cardiac (IC) ECG signals, and (e.g., at the same time) surface electrodes 38 are sensing the BS ECG signals. In other embodiments, sensing the IC ECG signals may be sufficient for performing the IRE ablation, so that surface electrodes 38 may be applied for other use cases.

In some embodiments, physician 30 may couple multiple electrodes 50 to a target tissue at the ablation site in heart 26. The target tissue is intended to be ablated by applying one or more IRE pulses via pairs of electrodes 50. Note that the IRE pulses may be applied to the target tissue multiple times, using any suitable pattern, during the IRE ablation procedure.

This particular configuration of system 20 is simplified for the sake of conceptual clarity and is shown by way of example, in order to illustrate certain problems that are addressed by embodiments of the present invention and to demonstrate the application of these embodiments in enhancing the performance of such an IRE ablation system. Embodiments of the present invention, however, are by no means limited to this specific sort of exemplary system, and the principles described herein may similarly be applied to other sorts of ablation systems.

Figure 2:
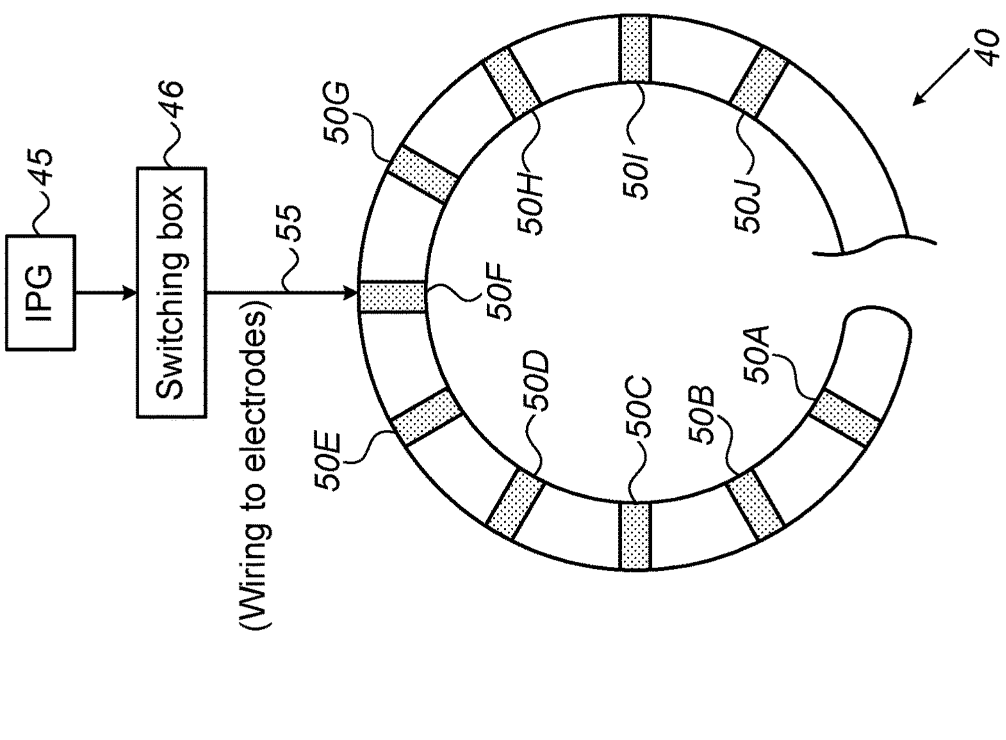
FIG. 2 is a schematic pictorial illustration of a tip section of an IRE catheter having multiple electrodes, and architecture for applying IRE pulses to selected electrodes thereof, in accordance with an exemplary embodiment of the present invention.

Applying Irreversible Electroporation Pulses To Tissue In Accordance With A Predefined Pattern FIG. 2 is a schematic pictorial illustration of tip section 40, and an architecture for applying IRE pulses to selected electrodes 50, in accordance with an exemplary embodiment of the present invention.

In the example of FIG. 2, tip section 40 comprises ten electrodes 50, referred to herein as electrodes 50A, 50B, 50C, 50D, 50E, 50F, 50G, 50H, 50I and 50J, coupled to tip section 40 along the lasso described in FIG. 1 above.

In some embodiments, IPG 45 applies the BAPs to switching box 46, which is electrically coupled to each of electrodes 50A-50J via a respective wire 55, or using any other suitable connection.

In some embodiments, based on the aforementioned mapping of heart 26, processor 41 and/or physician 30 may select from the aforementioned one or more predefined patterns of the IRE ablation protocol stored in memory 48, the most suitable predefined pattern for treating the arrhythmia detected in heart 26.

An example of a predefined pattern is shown in Table 1 below:

TABLE 1

Predefined pattern of EP by time slot

| Time Slot | Energized EP |
|---|---|
| 1 | 50E-50G |
| 2 | 50F-50H |
| 3 | 50A-50C |
| 4 | 50B-50D |
| 5 | Empty |
| 6 | Empty |
| 7 | 50G-50I |
| 8 | 50H-50J |
| 9 | 50C-50E |
| 10 | 50D-50F |

As shown in Table 1, each time slot defines an electrode-pair (EP), which receives bipolar ablation pulses (BAPs) generated by IPG 45 and routed to the respective EP via switching box 46.

In some embodiments, all EPs have the same inter-electrode distance. For example, the distance between electrodes 50E and 50G of time slot 1 is similar to the distance between electrodes 50F and 50H of time slot 2, and to the distance between electrodes 50C and 50E of time slot 9.

In some embodiments, at least some of electrodes 50 are used more than one time in different time slots of the same predefined pattern, but is paired with a different electrode in different time slots. For example, electrode 50C is paired with electrode 50A in time slot 1, and with electrode 50E in time slot 9. Moreover, as shown in Table 1, at least one time slot is positioned, in the predefined pattern, between two time slots having a common electrode.

In some embodiments, the time slots are applied sequentially to the ablated tissue, but in other embodiments, two or more time slots may be applied at the same time or with some overlap in timing.

In some embodiments, each time slot defines a waveform of one or more BAPs that are applied in bursts, to the tissue by the respective EP. In the present example, the waveform comprises ten pulses of about 5 microseconds each, applied at 200 KHz, and the time slot is concluded by a time gap of about 0.5 millisecond (msec) typically but not necessarily scheduled after the tenth pulse. Moreover, all the time slots of Table 1 are using the same waveform described above.

In the context of the present disclosure and in the claims, the terms "about" or "approximately" for any numerical values or ranges indicate a suitable dimensional tolerance that allows the part or collection of components to function for its intended purpose as described herein.

In some embodiments, the predefined pattern comprises a periodic set of the time slots. In other words, after concluding time slot 10 and the time gap, the predefined pattern is repeated one or more times, so as to complete the required amount of ablation energy applied to the ablated tissue. Note that the number of repetitions may be calculated based on the electrical mapping and the aforementioned ablation protocol. As described above, the total duration of each time slot is slightly longer than about 0.5 msec, and therefore, the total duration, also referred to herein as the cycle length, of the predefined pattern, is slightly longer than 5 msec.

In such embodiments, each electrode-pair of the predefined pattern has a duration slightly longer than 5 milliseconds for cooling before receiving the next waveform of ten BAPs, thereby preventing overheating of the respective electrodes, and may also prevent uncontrolled damage to the section of tissue located between the electrodes of the respective pair.

In some embodiments, the predefined pattern of Table 1 has time slots 5 and 6 that are empty. In the context of the present disclosure and in the claims, the term "empty" refers to not applying any BAP to any EP of electrodes 50 of catheter tip 40. Note that in the present example, the time gap of 0.5 msec is retained also in the empty time slots.

Note that the EPs of the predefined pattern are interleaved between the time slots. For example, electrode 50F of time slot 2 is positioned (along catheter tip 40) between electrodes 50E and 50G of time slot 1.

In other embodiments, the ablation protocol may comprise a predefined pattern having all time slots filled with respective EPs receiving one or more BAPs from IPG 45. In other words, without empty time slots.

In yet other embodiments, physician 30 and/or processor 41 may skip a time slot, e.g., by not energizing the EP defined in the time slot, and thereby may shorten the cycle length of the predefined pattern.

In alternative embodiments, each time slot may comprise more than one waveform with a time gap between adjacent waveforms.

This particular time slot configuration and order of the predefined pattern of Table 1 are shown by way of example, in order to illustrate certain problems that are addressed by embodiments of the present invention and to demonstrate the application of these embodiments in enhancing the performance of such an IRE ablation protocol. Embodiments of the present invention, however, are by no means limited to this specific sort of example predefined pattern, and the principles described herein may similarly be applied to other sorts of predefined pattern and/or ablation protocols.

Figure 3:
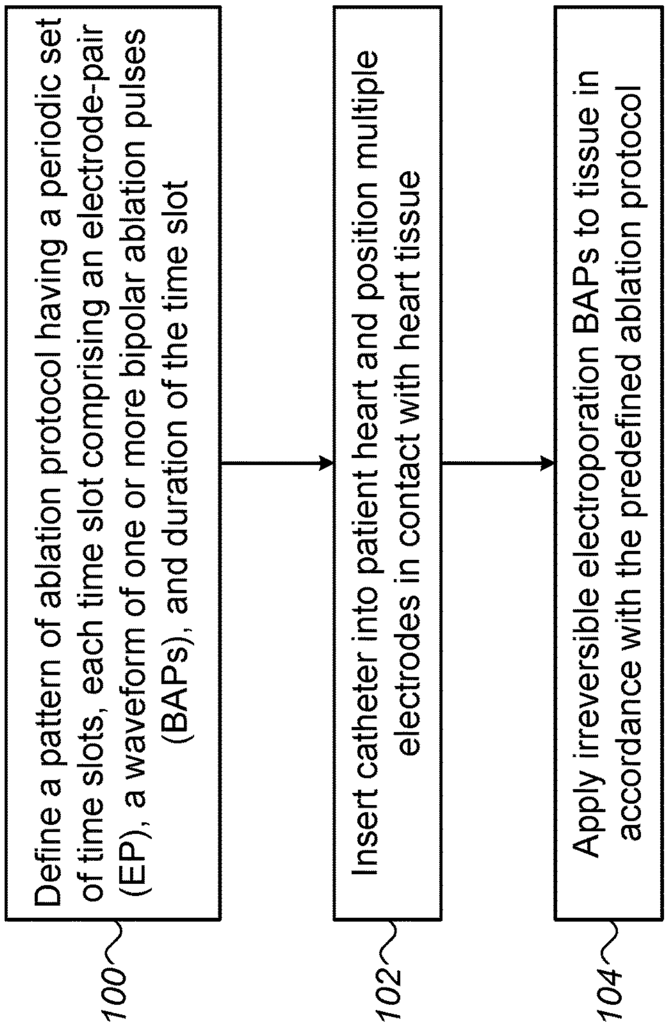
FIG. 3 is a flow chart that schematically illustrates a method for applying bipolar IRE ablation pulses to tissue, in accordance with an exemplary embodiment of the present invention.

FIG. 3 is a flow chart that schematically illustrates a method for applying bipolar IRE ablation pulses to ablated tissue, in accordance with an embodiment of the present invention. The method begins at an ablation protocol definition step 100, with defining a pattern of ablation protocol having a periodic set of time slots. Each time slot comprising an electrode-pair (EP), a waveform of one or more bipolar ablation pulses (BAPs), and duration of the time slot. As described in FIG. 2 above, the time slot may comprise a time gap scheduled before or after the one or more BAPs of the waveform.

At a catheter insertion step 102, physician 30 inserts catheter tip 40 of catheter 21 into heart 26 and positions multiple electrodes 50 in contact with the target tissue, as described in FIG. 1 above.

At a tissue ablation step 104 that concludes the method, irreversible electroporation (IRE) bipolar ablation pulses (BAPs) are applied to the target tissue in accordance with the predefined pattern of the ablation protocol described in step 100 above, and in greater detail in FIG. 2 above. Note that the predefined pattern is periodic, such that the set of time slots repeats after concluding the cycle of time slots defined in the pattern. The number of repetitions is defined based on the ablation protocol and the electrical mapping of heart 26, such that, in case of multiple repetitions, the method terminates after concluding the last repetition, and physician 30 retracts catheter tip 40 out of patient 28.

Although the embodiments described herein mainly address irreversible electroporation of patient heart, the methods and systems described herein can also be used in other applications, such as but not limited to renal ablation, liver ablation, treatment of lung cancer or in ablation of any other suitable organ.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method comprising:

receiving a predefined pattern comprising:

(1) a set of time slots, wherein each of the time slots defines: (a) a single electrode-pair (EP) from a plurality of electrodes arranged along a ring-shaped distal end of an intrabody probe, (b) a duration, and (c) a waveform of one or more bipolar ablation pulses (BAPs) to be delivered by the single EP during the duration of the time slot, wherein the single EPs in at least two of the time slots of the set of time slots include a common electrode of the plurality of electrodes and are separated by at least one time slot from the set of time slots, and wherein the predefined pattern is configured to generate electric fields that span the ring-shaped distal end of the intrabody probe with selected spatial overlaps in the electric fields generated, and (2) an empty time slot during which no BAP is applied to any single EP from the plurality of electrodes;

causing, in response to receiving user instructions to ablate at a target intrabody location, each waveform to be generated based on the predefined pattern; and causing the waveforms to be delivered to the single EPs as defined by the predefined pattern.

2. The method according to claim 1, comprising repeating delivery of the waveforms to the plurality of electrodes based on the predefined pattern.

3. The method according to claim 1, wherein the waveform of each time slot of the set of time slots is delivered successively to the single EPs associated with each time slot.

4. The method according to claim 1, wherein the waveforms of two or more time slots of the set of time slots are delivered to the single EPs associated with the two or more time slots, respectively, with a defined temporal overlap.

5. The method according to claim 1, wherein the waveforms of two or more time slots of the set of time slots are delivered simultaneously to the single EPs associated with the two or more time slots.

6. The method according to claim 1, scheduling a time gap between repetitions of the predefined pattern and repeating generation of each waveform generated based on the predefined pattern after a lapse of the time gap.

7. The method according to claim 1, wherein the BAPs comprise irreversible electroporation (IRE) BAPs.

8. The method according to claim 1, wherein the predefined pattern includes a first time slot of the set of time slots including a first electrode of the plurality of electrodes and a second electrode of the plurality of electrodes and a second time slot of the set of time slots including the first electrode and a third electrode of the plurality of electrodes.

9. A system comprising:

a processor; and a non-transitory computer readable medium storing a plurality of instructions, which when executed, cause the processor to:

receive a predefined pattern comprising:

(1) a set of time slots, wherein each of the time slots defines: (a) a single electrode-pair (EP) from a plurality of electrodes arranged along a ring-shaped distal end of an intrabody probe, (b) a duration, and (c) a waveform of one or more bipolar ablation pulses (BAPs) to be delivered by the single EP during the duration of the time slot, wherein the single EPs in at least two of the time slots of the set of time slots include a common electrode of the plurality of electrodes and are separated by at least one time slot from the set of time slots, and wherein the predefined pattern is configured to generate electric fields that span the ring-shaped distal end of the intrabody probe with selected spatial overlaps in the electric fields generated, and (2) an empty time slot during which no BAP is applied to any single EP from the plurality of electrodes;

cause, in response to user instructions to ablate at a target intrabody location, waveforms to be generated based on the predefined pattern; and cause the waveforms to be delivered to the single EPs as defined by the received predefined pattern.

10. The system according to claim 9, wherein the plurality of instructions further cause the processor to repeat delivery of the waveforms to the plurality of electrodes based on the predefined pattern.

11. The system according to claim 9, wherein the plurality of instructions further cause the processor to successively deliver the waveform of each time slot to the single EPs associated with each time slot.

12. The system according to claim 9, wherein the plurality of instructions further cause the processor to deliver the waveforms of two or more time slots of the set of time slots to the single EPs associated with the two or more time slots, respectively, with a defined temporal overlap.

13. The system according to claim 9, wherein the plurality of instructions further cause the processor to simultaneously deliver the waveform of two or more time slots of the set of time slots to the single EPs associated with the two or more time slots.

14. The system according to claim 9, wherein the plurality of instructions further cause the processor to schedule a time gap between repetitions of the predefined pattern to provide instructions to repeat generation of each waveform generated based on the predefined pattern after a lapse of the time gap.

15. The system according to claim 9, wherein the BAPs comprise irreversible electroporation (IRE) BAPs.

16. The system according to claim 9, wherein the predefined pattern includes a first time slot of the set of time slots including a first electrode of the plurality of electrodes and a second electrode of the plurality of electrodes and a second time slot of the set of time slots including the first electrode and a third electrode of the plurality of electrodes.

17. A computer program product, comprising a non-transitory computer-readable medium having computer-readable program code embodied therein to be executed by one or more processors, the program code including instructions to:

receive a predefined pattern comprising:

(1) a set of time slots, wherein each of the time slots defines: (a) a single electrode-pair (EP) from a plurality of electrodes arranged along a ring-shaped distal end of an intrabody probe, (b) a duration, and (c) a waveform of one or more bipolar ablation pulses (BAPs) to be delivered by the single EP during the duration of the time slot, wherein the single EPs in at least two of the time slots of the set of time slots include a common electrode of the plurality of electrodes and are separated by at least one time slot from the set of time slots, and wherein the predefined pattern is configured to generate electric fields that span the ring-shaped distal end of the intrabody probe with selected spatial overlaps in the electric fields generated, and (2) an empty time slot during which no BAP is applied to any single EP from the plurality of electrodes;

cause waveforms to be generated based on the predefined pattern in response to instructions to ablate at a target intrabody location; and cause the waveforms to be delivered to the single EPs as defined by the predefined pattern.

18. The computer program product according to claim 17, the program code including further instructions to repeat delivery of the waveforms to the plurality of electrodes based on the predefined pattern.

19. The computer program product according to claim 17, wherein the waveform of each time slot of the set of time slots is delivered successively to the single EPs associated with each time slot.

20. The computer program product according to claim 17, wherein the waveforms of two or more time slots of the set of time slots are delivered to the single EPs associated with the two or more time slots, respectively, with one of: i) a defined temporal overlap; ii) or a time gap between repetitions of the predefined pattern such that the generation of each waveform generated based on the predefined pattern are repeated after a lapse of the time gap.

* * * * *